United States Patent
Mackwood Ling et al.

(10) Patent No.: US 6,241,772 B1
(45) Date of Patent: Jun. 5, 2001

(54) PLUGGING AND CENTRALIZED DEVICE FOR LOCATING THE STEM OF A PROSTHESIS

(75) Inventors: Robin Sydney Mackwood Ling, Dartmouth; Graham Allan Gie, Yeoford; Andrew John Timperley, Exeter, all of (GB); Denis Pichon, Bieville-Beuville; John Andrew Storer, Bayeux, both of (FR)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/323,615

(22) Filed: Jun. 1, 1999

(30) Foreign Application Priority Data

Jun. 4, 1998 (GB) .................................................. 9812070

(51) Int. Cl.[7] ........................................................ A61F 2/36
(52) U.S. Cl. ........................................................ 623/23.15
(58) Field of Search ................................ 623/23.15, 22.4, 623/22.41, 22.42, 22.43, 22.44, 22.45, 22.46, 23.21, 23.22, 23.26, 23.46; 606/95

(56) References Cited

U.S. PATENT DOCUMENTS

| | | | |
|---|---|---|---|
| 3,712,301 | * | 1/1973 | Sarnoff ................................ 604/136 |
| 3,793,650 | * | 2/1974 | Ling et al. ........................ 623/23.46 |
| 3,982,613 | * | 9/1976 | Wood ................................ 190/58 B |
| 4,067,333 | * | 1/1978 | Reinhardt et al. .................... 604/191 |
| 4,753,657 | * | 6/1988 | Lee et al. ........................... 623/16.11 |
| 4,783,192 | * | 11/1988 | Wroblewski et al. ............ 623/23.21 |
| 5,002,580 | * | 3/1991 | Noble et al. ...................... 623/23.23 |
| 5,057,101 | * | 10/1991 | Dorr et al. ........................ 623/23.23 |
| 5,092,892 | | 3/1992 | Ashby . |
| 5,108,437 | * | 4/1992 | Kenna ............................... 623/16.11 |
| 5,171,289 | * | 12/1992 | Tornier ............................. 623/22.14 |
| 5,658,351 | * | 8/1997 | Dudasik et al. .................. 623/23.48 |
| 5,725,500 | * | 3/1998 | Micheler ............................... 604/82 |
| 5,766,178 | | 6/1998 | Michielli et al. . |
| 5,984,968 | * | 11/1999 | Park ................................. 623/16.11 |
| 5,997,581 | * | 12/1999 | Khalili ............................. 623/23.48 |

FOREIGN PATENT DOCUMENTS 2 017 503  10/1979  (GB) .
2 047 541  12/1980  (GB) .

* cited by examiner

*Primary Examiner*—Gene Mancene
*Assistant Examiner*—Eduardo C. Robert
(74) *Attorney, Agent, or Firm*—Lerner, David, Littenberg, Krumholz & Mentlik, LLP

(57) ABSTRACT

A device for plugging the medullary canal of a bone to prevent the passage of locating cement and for centralising or guiding the stem of a prosthesis comprising a main body portion adapted to engage the wall of the canal to act as a plug and having a centralising or guide opening to receive the stem of the prosthesis.

17 Claims, 3 Drawing Sheets

PLUGGING AND CENTRALIZED DEVICE FOR LOCATING THE STEM OF A PROSTHESIS

BACKGROUND OF THE INVENTION

1. Field of the Invention

This invention relates to a plugging and centralising device for locating the stem of a prosthesis.

2. Description of the Prior Art

When using cement to locate the stem of a prosthesis in an medullary canal it is usual to plug the lower end of the canal to prevent cement extending along it beyond the stem of the prosthesis.

Such plugs are well known, for example as shown in GB 2 017 503 which shows a plug with ranks of resilient lugs which jam against the side wall of the cavity to prevent the bone cement from escaping downwards. Another type of plug is shown in GB 2 047 541 which has a mid-portion which serves as a seal against the walls of the canal and an upper portion which is open ended to define a recess formed by a series of petals which are intended to prevent extrusion of the plug back out of the open canal. Another plug is show in U.S. Pat. No. 5,766,178 which has deformable flanges.

It is also known to provide a centraliser for the distal end of the stem of a prosthesis, for example as shown in U.S. Pat. No. 5,092,892 in which there are resiliently deformable fins which engage the wall of the canal and an annular body portion which locates the tip end of the stem of the prosthesis. Another type of centraliser is shown in GB 1 409 053 which has an annular base member with a number of spring members extending therefrom. The annular portion receives the free end of the stem and slides only part way along it and the spring members act to centraliser the stem in the canal.

Plugs and centralisers are frequently used together.

SUMMARY OF THE INVENTION

The present invention is intended to provide a single device which will act as a plug and a centraliser or guide and which is easy to manufacture and use.

According to the present invention a device for plugging the medullary canal of a bone to prevent the passage of locating cement and for centralising or guiding the stem of a prosthesis comprises a main body portion adapted to engage the wall of the canal to act as a plug and having a centralising or guide opening to receive the stem of the prosthesis.

Thus, this device can replace the combination of known types of plugs and centralisers.

In one preferred embodiment the centralising or guide opening is adapted to engage and locate the stem at a position between up to one half of its length from its distal end.

In another alternative embodiment the centralising or guide opening is adapted to engage and locate the distal end of the stem of the prosthesis.

The opening may be constructed to extend through the main body portion and be adapted to allow the stem, when in place, to protrude beyond it.

In another construction the main body portion can include a cup, the open end of which provides the opening, the open end being adapted to engage the stem and the cup being deep enough to accept subsequent further inward movement of the stem.

The open end or ends of the opening can be reinforced.

The device can be made from any convenient material, for example metal but is preferably made from a synthetic material, for example polymethylmethacrylate (PMMA).

In any case, the material used is preferably resilient.

BRIEF DESCRIPTION OF THE DRAWINGS

The invention can be performed in various ways and two embodiments will now be described by way of example and with reference to the accompanying drawings in which.

DESCRIPTION OF THE PREFERRED EMBODIMENTS

Figure 1:
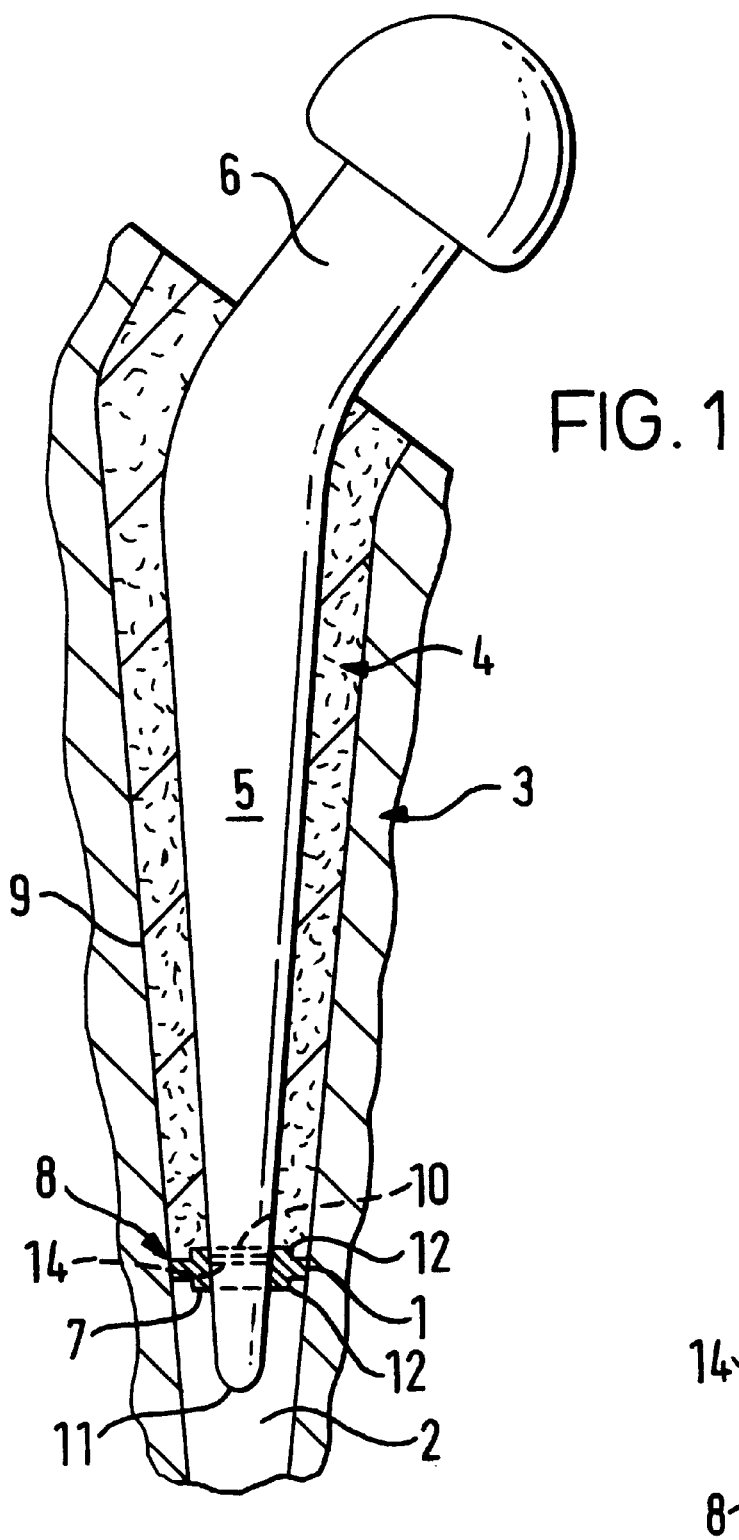
FIG. 1 is a cross-sectional side elevation of the device according to the invention located on the stem of a prosthesis in an medullary canal.

As shown in FIG. 1 a device 1 for plugging the medullary canal 2 of a bone 3 to prevent the passage of locating cement 4 and for centralising the stem 5 of a prosthesis 6 comprises a main body portion 7 having a circumferential outer wall 8 which is shaped and adapted to engage the wall 9 of the medullary canal 2.

The main body portion 7 is provided with an opening 10 which extends right through the main body portion and is dimensioned and adapted to allow the stem 5, when in place, to protrude beyond it as shown in FIG. 1. The opening 10 is adapted to engage the stem 5 at a point spaced away from its tip 11. A reinforcing collar 12 surrounds each of the open ends of the opening 10 to provide reinforcement.

The device can be made from any convenient material and is preferably made from a synthetic material, for example polymethlylmethacrylate (PMMA).

The combined plug and centraliser can be made from a resilient material so that it allows a good sealing fit against the walls 9 of the canal 2 and against the stem 5 of a prosthesis 6.

When the cement is loaded into the canal 2 prior to insertion of the stem 5 and during insertion thereof a small amount of cement may be lost through the opening 10 before the stem is located in it.

In order to prevent the cement loss the opening 10 can be provided with a membrane 14 which closes the opening and which is pierced by the tip 11 of the stem 5 when it is inserted.

Figure 2:
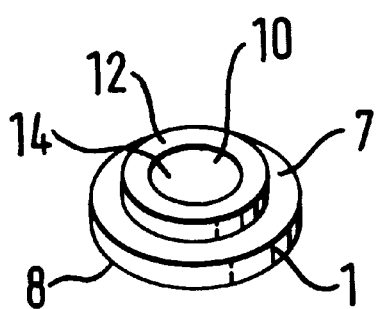
FIG. 2 is an isometric view of the device according to the invention as used in FIG. 1.

In the construction shown in FIGS. 1 and 2 the opening 10 is substantially circular to accept a circular stem 5 but in constructions where the lower end of the stem is some other shape, for example it may have flat sides, the opening 10 is shaped appropriately.

The opening can initially be straight sided if the material is resilient enough to accept the deformation of the tapered end of the stem. Alternatively the opening 10 can be preformed in a tapered shape.

Figure 3:
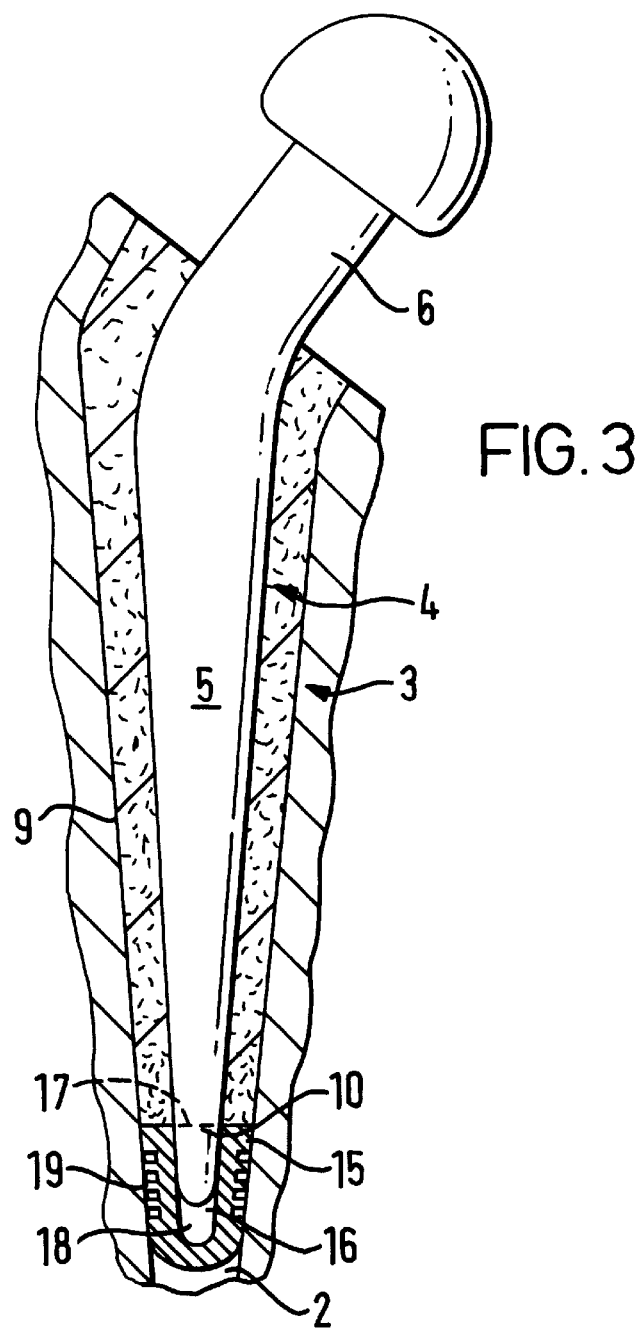
FIG. 3 is a cross-sectional side elevation of another construction according to the invention in place on a prosthesis in an medullary canal.

FIG. 3 shows another construction according to the invention and in which the same reference numerals are used to indicate similar parts. In this construction the body portion 15 includes a cup 16, the opening end 17 of which provide the entry opening 10. This open end 17 is adapted to engage the stem 5 and the cup 16 is deep enough to provide a void 18 beneath the stem 5 and which can accept subsequent further inward movement of the stem if it is of the collarless type.

In order to assist location the outer sides of the cup are provided with retention flanges 19 which can act to assist in gripping the sides 9 of the canal 2. This construction can, of course, be made solid provided it is resilient enough to accept the deformation as it is placed in position in the canal 2. Once again the shape of the cup will be appropriate for use with the stem 5 of the prosthesis in which it is intended to be used.

With this construction no cement is lost through the opening 10 when the stem is inserted.

In an alternative construction (not shown) but which is generally similar to that shown in FIG. 3 the engagement wall of the device could be rigid rather than resilient and the canal wall could be appropriately prepared to accommodate it.

Figure 4:
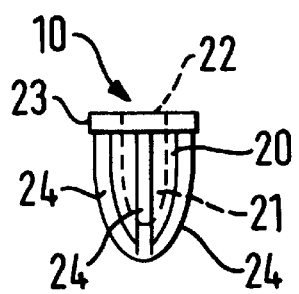
FIGS. 4 and 5 are side elevations of further alternative construction according to the invention; and, FIGS. 6 and 7 are elevations of other alternative constructions.

FIG. 4 shows another construction according to the invention in which the main body portion 20 includes a cup 21 the open end 22 of which provides the entry opening 10 as with the construction shown in FIG. 3 but this open end is adapted to engage the stem 5 and the cup 21 is deep enough to provide a void beneath the stem 5 and which can accept subsequent further inward movement of the stem if it is of the collarless type. In this construction the proximal end of the plug is formed with an engagement rim 23 adapted to engage the wall 9 of the canal 2. Beneath this rim the general diameter of the main body 20 is reduced but is provided with four projecting wings 24 which are dimensioned so that they act to centralise the stem at its distal end. The wings 24 can be rigid to engage a prepared portion of the canal 2 or can be made to accommodate the narrowing in the canal 2 by compression or flexing. The rim 23 provides sufficient plugging effect.

Figure 5:
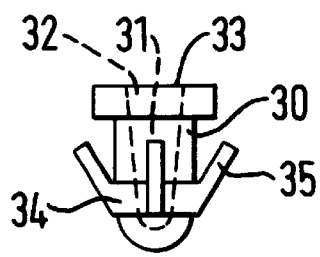

FIG. 5 shows a construction in which the main body portion 30 includes a cup 31 the open end 32 of which provides an entry opening 33 which is adapted to engage the stem 5 and the cup 31 is again deep enough to accommodate inward movement of the stem in a similar manner to the construction shown in FIG. 4. With this arrangement however the spacer is formed as an annulus 34 on which are mounted a number of centralising arms 35. The arms can be constructed so that they will flex to centralise the plug as it is moved down the canal 2. The annulus 34 can be made of the same material as the main body portion 30 or it can be a different material and may be metal or a plastics material. The centralising arms 35 can be replaced by, for example, wings or any other element which will provide the necessary centralising effect.

The material and dimensions can be arranged so that the annulus 34 can either be fitted immediately prior to use or it could be assembled during initial manufacture.

Figure 6:
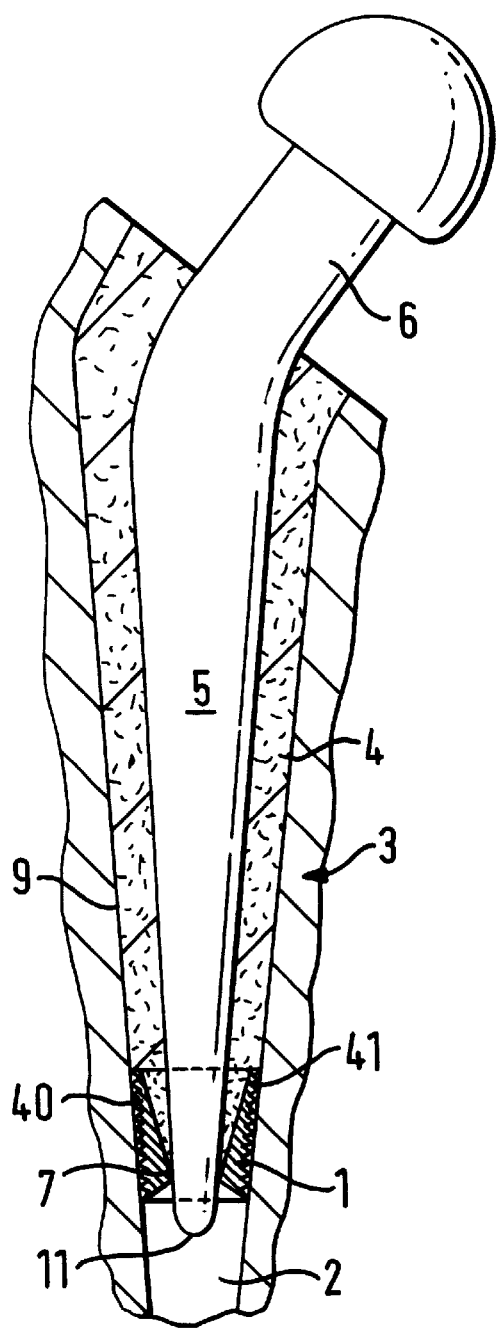

FIG. 6 shows another construction of plug and centraliser in which the same reference numerals are again used to describe similar parts but in this construction the upper part of the opening 40 is tapered which assists entry of the stem 5. The sides of the main body 7 are provided with corrugations 41 to assist in holding the plug against the wall of the canal 9. In the construction shown the tip 11 of the stem 5 is exposed but if desired a cup, similar to that shown in FIGS. 3, 4 and 5, could be provided to accommodate downward movement of the stem 5 after fitting and for the same reasons.

Figure 7:
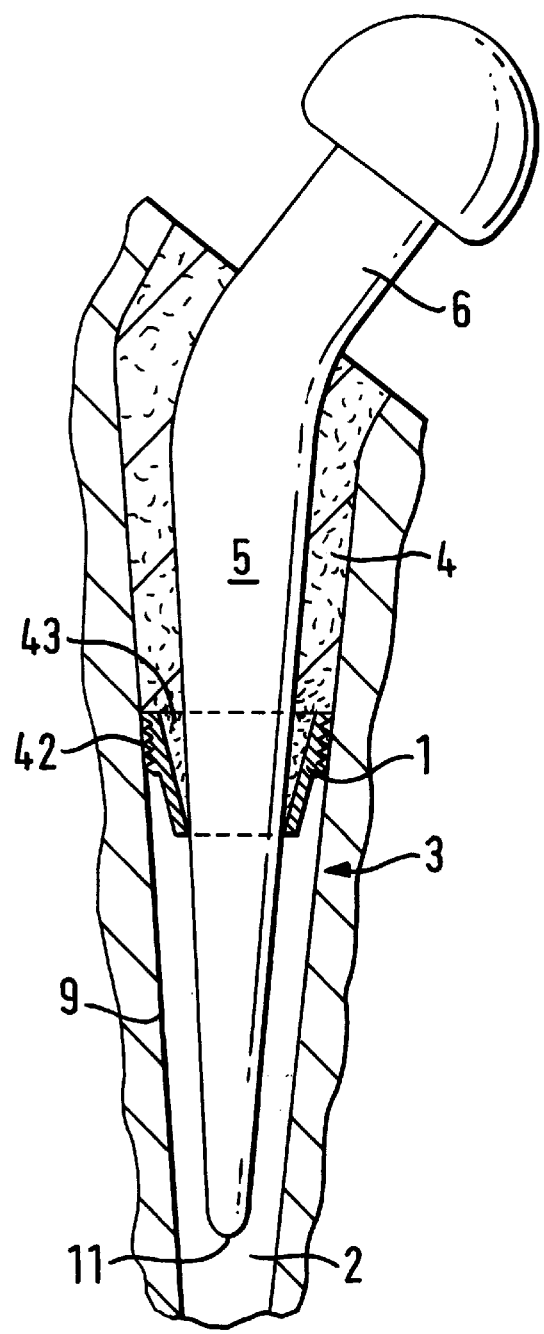

FIG. 7 shows a construction in which the dimensions of the plug and centraliser or guide are determined so that the device will fit onto the stem 5 at a point up to half the length of the stem. Thus, the arrangement is such that only the proximal two thirds, or even the proximal half of the stem, is engaged within the cement 4.

The construction of the plug could be as set out in any of the preceding examples but it would of course be impractical to provide a cup in the opening but the methods of locating the plug in position could take any convenient form. In the construction shown in FIG. 7 the outer surface of the main body is provided with corrugations 42 and the opening 43 is again tapered to assist in locating the stem 5 when it is entered. A diaphragm (not shown) could again be employed across the opening 43 with any of the constructions described.

There are advantages with the construction shown in FIG. 7 as far as load transmission is concerned. The problem with regard to making certain that the surgeon can get the tip of the stem to engage in the central part of the device and thus pass through, for example, the membrane is solved by making the device in construction rather deeper and including the tapered entrance to the opening so that the taper will automatically guide the tip of the stem into the aperture in the device.

It will be obvious that the aperture has to be appropriately shaped according to the rough level in the canal that the device is to be placed. A close fit between the margins of the stem and the walls of the device is not particularly necessary because the acrylic cement 4 would itself seal any potential gaps, particularly if there is a tapering entrance to the device.

As tapered polished stems are used on this type of prosthesis it is unlikely that debris will find its way down around the stem between the stem and the cement and to the distal part of the medullary canal which is not filled with cement. This type of arrangement has the added advantage of potentially significantly reducing the amount of cement that is needed for a given femur.

It will be clear that in all the constructions described above the shape of the opening that is covered by the membrane or even which is open can be varied according to the stem geometry and the rough site of the canal in which it is proposed to place the plug.

The plug and centraliser can be made in various sizes suitable for the requirements of the bone and canals concerned.

What is claimed is:

1. A bone plug for plugging a medullary canal of a bone to prevent a passage of bone cement beyond the plug and for centralizing or guiding a stem of a prosthesis, the stem having a tip for insertion into the canal from an open end of the bone along a longitudinal axis of the canal, said plug comprising:

a main body portion having an inner surface and an outer surface for sealingly engaging an inner wall of the bone canal, the outer and inner surfaces forming a wall surrounding an opening to receive the stem, said opening having a membrane extending thereacross to seal the opening, the membrane being piercable by said stem tip upon movement in said insertion direction.

2. The plug of claim 1 in which the opening extends through the main body portion and has a cross-section sized to engage said stem in a manner to allow the stem when in place to protrude beyond it.

3. The plug as claimed in claim 2 in which said opening engages the stem at a position between up to one half of its length from its tip to an end thereof adjacent said open bone end opposite said tip.

4. The plug as claimed in claim 2 in which the centralizing or guide opening is adapted to engage and locate the distal end of the stem of the prosthesis.

5. The plug as claimed in claim 1 in which the plug wall has an open end or ends which are reinforced.

6. The plug as claimed in claim 1 in which the opening inner surface is tapered inwardly along said longitudinal axis in the direction of insertion of said stem.

7. The plug as claimed in claim 1 which is made from a synthetic material.

8. The plug as claimed in claim 7 in which the synthetic material is polymethylmethacrylate (PMMA).

9. The plug as claimed in claim 1 which is made from a resilient material.

10. The plug as claimed in claim 1 which is made from a resilient material.

11. The plug as claimed in claim 1 in which the opening inner surface is tapered inwardly along said longitudinal axis in the direction of insertion of said stem.

12. The plug as claimed in claim 1 in which the plug wall has an open end or ends which are reinforced.

13. A device for plugging the medullary canal of a bone and for guiding the insertion of a stem of a prosthesis into the canal, said stem having a tip for insertion into the canal from an open end thereof, said device comprising:

an annular body having an outer surface for engaging the inner wall of the canal and an inner surface defining an opening therethrough for engaging the stem, the inner surface tapering from a wider opening to a narrower opening in the direction of insertion of said stem into said canal, wherein the opening is provided with a piercable membrane which closes the opening prior to use, said membrane piercable by said stem tip upon insertion of said stem in said direction of insertion.

14. The device as claimed in claim 13 in which the opening extends through the main body portion and is adapted to allow the stem when in place to protrude beyond it.

15. The device as claimed in claim 13 in which the centralizing or guide opening is adapted to engage and locate the stem at a position between up to one half of its length from its distal end.

16. The plug as claimed in claim 13 which is made from a synthetic material.

17. The plug as claimed in claim 16 in which the synthetic material is polymetlhylmethacrylate (PMMA).

\* \* \* \* \*

UNITED STATES PATENT AND TRADEMARK OFFICE
CERTIFICATE OF CORRECTION

PATENT NO. : 6,241,772 B1
DATED : June 5, 2001
INVENTOR(S) : Mackwood Ling et al.

It is certified that error appears in the above-identified patent and that said Letters Patent is hereby corrected as shown below:

Title page,
Under item [54], Title, "CENTRALIZED" should read -- CENTRALIZING --.

Column 1,
Line 1, "CENTRALIZED" should read -- CENTRALIZING --.

Signed and Sealed this

Eleventh Day of December, 2001

*Attest:*

NICHOLAS P. GODICI
*Attesting Officer*   *Acting Director of the United States Patent and Trademark Office*